United States Patent [19]

Smith et al.

[11] Patent Number: 4,957,629

[45] Date of Patent: Sep. 18, 1990

[54] OBSTETRICAL FILTER AND TRAP

[76] Inventors: Lawrence M. Smith; Emily M. Smith, both of P.O. Box 5877, Bend, Oreg. 97708

[21] Appl. No.: 277,007

[22] Filed: Nov. 28, 1988

[51] Int. Cl.$^5$ .................. B01D 35/01; B01D 35/30
[52] U.S. Cl. .................. 210/443; 210/406; 210/456; 210/496; 55/185; 55/490; 604/406
[58] Field of Search ............ 210/440, 443, 444, 456, 210/350, 496, 406, 435; 604/406; 55/185, 490, 527

[56] References Cited

U.S. PATENT DOCUMENTS

| | | | |
|---|---|---|---|
| 723,556 | 3/1903 | Stewart | 210/443 |
| 1,679,033 | 7/1928 | Holmes | 210/447 |
| 2,381,354 | 8/1945 | Larson | 210/443 |
| 2,525,287 | 10/1950 | Cuno | 210/443 |
| 3,648,843 | 3/1972 | Pearson | 210/443 |
| 4,685,472 | 8/1987 | Muto | 210/451 |

Primary Examiner—W. Gary Jones
Attorney, Agent, or Firm—Jack E. Day

[57] ABSTRACT

A filter for obstetrical fluids and particulate matter having an enclosure containing a first chamber and a second chamber is disclosed. The first chamber has a solid partition forming first and second cavities in the first chamber. The first cavity has an inlet and the second cavity has an outlet. The second chamber contains a filter and the edge of the partition is pressed against the surface of the filter.

11 Claims, 1 Drawing Sheet

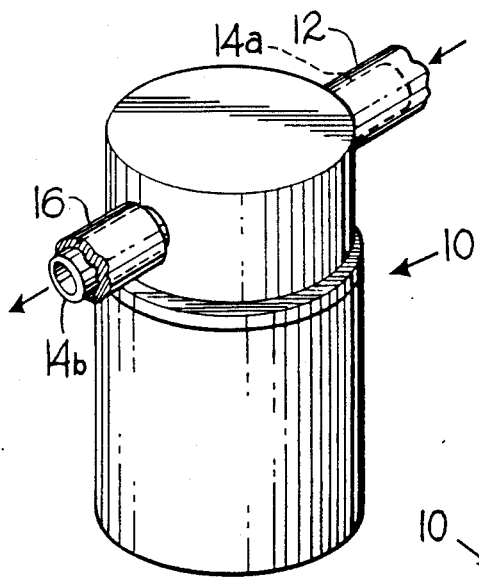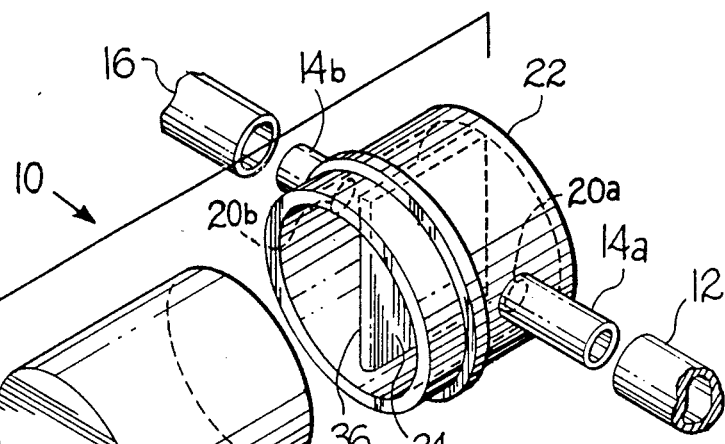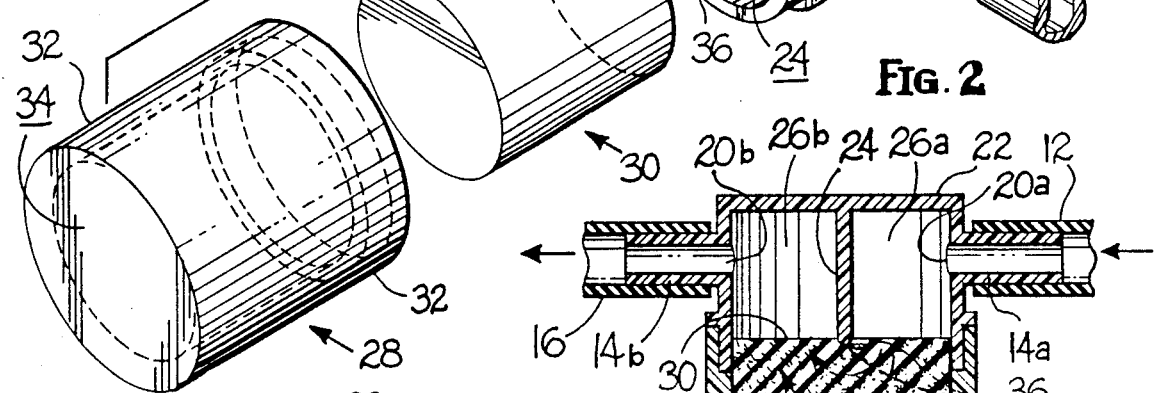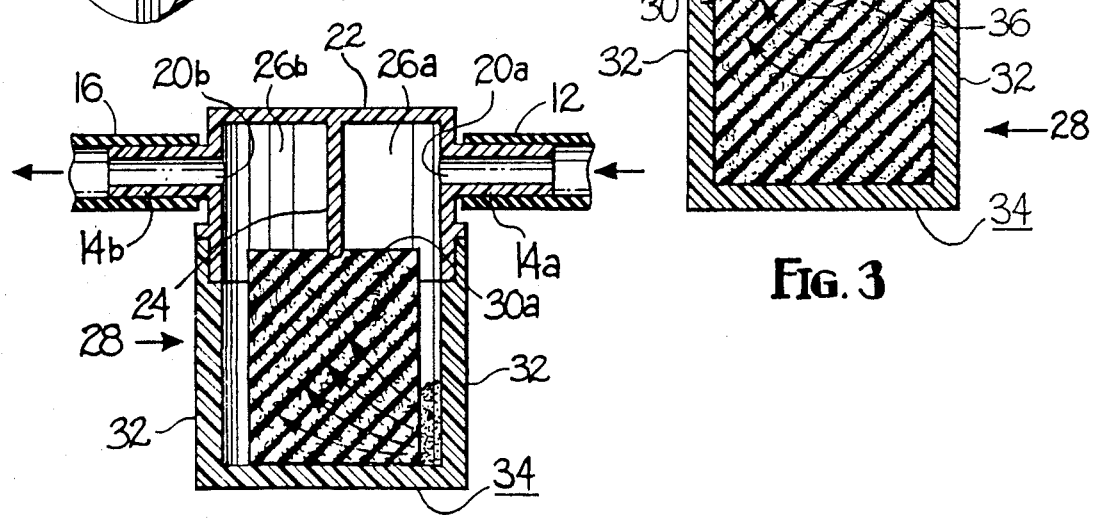

OBSTETRICAL FILTER AND TRAP

FIELD OF THE INVENTION

The present invention is, in general, a filter. It is, more specifically:

1. an improved fluid filter, for removing particulate matter from obstetrical fluids, particularly from amniotic fluid; and
2. a fluid trap, for removing fluids such as mucus and/or blood, from where it is unwanted, e.g., from a vacuum line, for example, to prevent it from entering and clogging a vacuum pump.

BACKGROUND OF THE INVENTION

It has been found that obstetrical fluids, particularly amniotic fluid and certain fractions thereof, are extremely useful in certain therapeutic applications, and it thus becomes important to collect and preserve it. However, the circumstances of its collection seldom permit any extensive processing at that time, and it becomes important to remove particulate matter therefrom before storing it for further processing at a more convenient time.

Further, it becomes important in vacuum-assisted births, to prevent fluids such as mucus and/or blood, from entering a vacuum pump, where they could clog the pump and reduce its effectiveness during critical procedures.

Little appears to have been done in this particular field, although the field of filters in general would appear to have some relevance thereto.

Holmes U.S. Pat. No. 1,679,033 discloses a filter for fluids, which appears to be highly similar to fuel filters from early automobiles. It has little relevance to the structure of the present invention.

Austrian Patent 167,986 also discloses a fuel filter, in which the fuel flows into an annular chamber from one side thereof, around a central cylindrical post and into the edges of a filter block which is inserted into the annular chamber over the exit passage. There is little relevance to the structure of the present invention.

Pearson U.S. Pat. No. 3,648,843 discloses a filter in which the principal novelty is the structure of the filter elements themselves. There is no relevance to the structure of the present invention.

Muto U.S. Pat. No. 4,685,472 discloses a biological specimen collector in which the closest resemblance to the structure of the present invention is the manner in which it can be dismantled. However, the internal structure of the present invention, which determines the working of the filter and is one of the features of novelty, is different than Muto.

BRIEF DESCRIPTION OF THE PRESENT INVENTION

The present invention includes a container or enclosure having a first chamber and a second chamber. The second chamber, which can be made removable from the first chamber, contains the actual filter means, which can be made replacable if desired. The first chamber is divided into a first cavity and a second cavity by a simple partition.

When used as a fluid filter, the fluid enters through an inlet means into the first cavity of the first chamber, and is diverted by the partition into and through the filter means, which fits snugly against the side-walls of the second chamber. It traverses said filter means in a generally U-shaped path, exiting into the second cavity of the first chamber and passing out through a second orifice into an outlet means, the flexible tubing attached thereto and to a collection receptacle, from which it is removed for further processing. When functioning as a fluid filter, the orientation of the filter is immaterial.

When used as a fluid trap, the filter is inserted in the vacuum system immediately preceding the vacuum pump and prevents unwanted fluids, such as blood and/or mucus contained in the evacuated gases, from entering therein, where they might clog the pump. In this use, the orientation of the filter is important, it being necessary that the first chamber be located substantially vertically above the second chamber. Also, the filter means is spaced away from the wall of the second chamber, at least in the portion directly below the first cavity, so that as blood and/or mucus is carried by the evacuated gases enter through the inlet means into the first cavity of the first chamber, it will fall downward to the floor of the second chamber, there to be absorbed by the filter means. The gases will be diverted by the partition downward into the space between the filter means and the wall of the second chamber, into the second cavity and through the outlet means to the vacuum pump.

When used as a fluid filter, it is necessary for the filter means to fit snugly into the lower chamber so that no fluid can avoid passing therethrough. The filter means can be a block of any of a number of standard biological filter materials.

When used as a fluid trap, it is necessary that the enclosure be oriented so that the first chamber is substantially vertically above the second chamber and that the filter means be spaced away from the wall of the second chamber, at least in the area below the inlet to the first cavity. Blood and/or mucus entering through the inlet means under the impetus of the evacuated gases will fall, under the influence of gravity, to the bottom of the second chamber and be absorbed into the filter means. It is desirable that the filter means be fabricated of a highly absorbent material so as to absorb all the unwanted matter.

The lower chamber of the enclosure can be made removable, if desired, to permit changing the filter means, or it can be fabricated with the upper chamber as a sealed unit, to be discarded when used.

BRIEF DESCRIPTION OF THE DRAWINGS

FIG. 1 is an oblique perspective view of the filter of the present invention, assembled.

FIG. 2 is an oblique perspective view of the present invention, in exploded view.

FIG. 3 is a profile view of the present invention used as a fluid filter, along the lines "3—3" of FIG. 2, in longitudinal section thereof.

FIG. 3A is a profile view of the present invention when used as a fluid trap, along the lines "3—3" of FIG. 2.

DETAILED DESCRIPTION OF THE PRESENT INVENTION

Turning now to FIG. 1, we see present invention 10 used either as a fluid filter or a fluid trap. When used as a fluid filter, obstetrical fluid flows, as indicated by the arrow, through flexible tubing 12 from the point of collection, into filter 10 through inlet means 14a, out of filter 10 through outlet means 14b through flexible tubing 16, as indicated by the arrow, and into some kind of receptacle (not shown) to be stored for later processing.

When used as a fluid trap to protect a vacuum system during vacuum-assisted births, for example, present invention 10 is placed immediately before the vacuum pump (not shown). Gas from a birthing-assistance device, such as a cranial bell or cup (not shown), is evacuated through tubing 12, into filter 10 through inlet means 14a, out of filter 10 through outlet means 14b via flexible tubing 16 into the vacuum pump, as indicated by the arrow. Unwanted fluids contained in the gases, which might clog the vacuum pump, are dropped to the bottom of filter 10 and are absorbed by the filter means contained therein.

FIG. 2 is an exploded view of the present invention, wherein the components and structure of filter 10 can be clearly and easily seen. Collection tube 12 attaches to filter 10 at inlet means 14a which opens, through first orifice 20a, into first chamber 22. Second orifice 20b leads through outlet means 14b to dispersion tube 16, and thence to a storage means for further processing, in the case of its use as a fluid filter, or to the vacuum pump when it is used as a fluid trap.

First chamber 22 is separated by solid partition 24 into first and second cavities 26a and 26b, respectively.

Filter 10 also includes second chamber 28 which, in one embodiment, is removable from first chamber 22. Second chamber 28 contains replaceable filter means 30 or 30a therein, as explained hereinafter, and can be assembled, by any of several well-known means, with first chamber 22. Lower edge 36 of partition 24 presses firmly upon filter means 30 or 30a, as disclosed in FIGS. 3 & 3A.

When used as a fluid filter, replaceable filter means 30 fits snugly into second chamber 28, with no voids or spaces between said filter means and wall 32 of second chamber 28, by means of which fluid might avoid passing through filter means 30.

When filter 10 is used as a fluid trap, highly absorbent replaceable filter means 30a is spaced away from the wall 32 of second chamber 28, so that mucus and/or blood can fall to the floor 34 thereof, as it enters first chamber 22 through orifice 20a, where it can be absorbed by filter means 30a. Evacuated gas entering first cavity 26a passes under partition edge 36 by means of the space between filter means 30 and wall 32 of second chamber 28 into second cavity 26b, from there to be evacuated.

In the fluid filter embodiment, the present invention is used as follows: filter means 30 is inserted into second chamber 28, fitting snugly therein against wall 32 thereof. Second chamber 28 is then affixed to first chamber 22, with partition edge 36 pressing tightly against the surface of filter means 30. Any standard collection device is connected by flexible tube 12 to inlet means 14a, and dispersion tube 16 is connected between some kind of collection receptacle, and outlet means 14b. When the obstetrical fluid begins to flow under the influence of the vacuum pump, it passes through inlet means 14a, through first orifice 20a into first cavity 24a of first chamber 22. Because of the presence of partition 26, the tight fit of the partition edge against the surface of filter means 30, and the snug fit of filter means 30 in second chamber 28, all of the fluid is forced to flow into and through filter means 30, where it will follow a more-or-less U-shaped path therethrough into second cavity 24b of first chamber 22, through orifice 20b into outlet means 14b and tubing 16.

The natural tendency of the fluid will be to take the shortest route through filter means 30. However, as particulate matter is captured by filter means 30, the area thereof which is immediately below partition 26 will become clogged and more resistant to the flow of said fluid therethrough, so that it will be forced to take a longer path through filter means 30, thereby improving its efficiency.

When used in the fluid trap embodiment, filter means 30a is inserted into second chamber 28, which is then affixed to first chamber 22. Filter means 30a is spaced from the wall 32 of second chamber 28, at least for a substantial area under orifice 20a. Any standard vacuum-assisted birthing device, such as a vacuum bell or cup (not shown) is connected by flexible tube 12 to inlet means 14a, and dispersion tube 16 is connected between the vacuum pump and outlet means 14b. When the gas begins to be evacuated from the birthing device, it will often contain droplets of blood and/or mucus which could clog or otherwise interfere with the operation of the vacuum pump. As these enter into first cavity 26a of first chamber 22 through inlet means 14a, they will drop to floor 36 of second chamber 28 and be absorbed by filter means 30a. The evacuated gases, on the other hand, will pass through the spaces between filter means 30a and sides 32, under partition edge 36 into second cavity 26b and out through outlet means 14 b.

The structure of the present invention lends itself to being fabricated in a variety of forms. For example, using modern materials, it could be economically produced in a simple "throw-away" version, where enclosure 10 is not separable into first chamber 22 and second chamber 28. This embodiment would be useful in emergency vehicles or smaller hospitals where manpower for assembling, disassembling and sterilizing, is short. On the other hand, it could be produced in a more permanent, reusable form, of sterilizable materials and with replaceable filter means, being sterilized between each use.

It will be readily seen by those skilled in the art that the present InventIon could be produced in a variety of forms and structures, without departing from the spirit or intent of the structure herein disclosed.

The terms and expressions which have been employed in the foregoing specification are used therein as terms of description and not of limitation. For example, except where specifically so identified, the terms "upper", "lower", "downward", "upward" or the like, are not to be construed as physical positions or directions, but only as individual elements, or relations between elements, of a structure. There is no intention, in the use of such terms and expressions, of excluding equivalents of the features shown and described, or portions thereof, it being recognized that the scope of the invention is defined and limited only by the claims which follow.

What I claim as my invention is:

1. A filter for obstetrical fluids and particulate matter, comprising:
   a. an enclosure containing a first chamber and a second chamber;
      1. said first chamber having therein:
         A. a solid partition having an edge, said partition forming first and second cavities in said first chamber;
            I. said first cavity having an inlet thereinto;
            II. said second cavity having an outlet therefrom;

2. said second chamber containing a filter means having a surface thereon; and
3. said edge of said partition pressing against said surface of said filter means.

2. The filter of claim 1, wherein said filter means fits snugly in said second chamber.

3. The filter of claim 1, wherein said first chamber is positioned substantially vertically above said second chamber, and said filter means is spaced away from the sidewall of said second chamber.

4. A filter for obstetrical fluids and particulate matter, comprising:
 a. an enclosure containing a first chamber and a second chamber;
  1. said first chamber having therein:
   A. a solid partition having an edge, said partition forming first and second cavities in said first chamber;
    I. said first cavity having an inlet thereinto;
    II. said second cavity having an outlet therefrom;
  2. said second chamber wholly occupied by filter means having a surface; and
  3. said edge of said partition pressing against said surface of said filter means, forcing all of said fluid to flow through said filter means.

5. The filter of claim 1, 2, 3, 4, wherein said enclosure is separable.

6. The filter of claim 1, 2, 3, 4, wherein said enclosure is separable into said first chamber and said second chamber.

7. The filter of claim 1, 2, 3, 4, wherein said first cavity is adjacent to said second cavity in said first chamber.

8. The filter of claim 1, 2, 3, 4, wherein said filter means is replacable.

9. A filter for obstetrical fluids and particulate matter, comprising:
 a. an enclosure separable into a first chamber and a second chamber;
  1. said first chamber having therein:
   A. a solid partition having an edge, said partition forming first and second adjacent cavities in said first chamber;
    I. said first adjacent cavity having inlet means thereinto;
    II. said second adjacent cavity having outlet means therefrom;
  2. said second chamber removably receiving replacable filter means having a surface thereon; and
  3. said edge of said partition pressing against said surface of said replacable filter means when said first and said second chambers are assembled to form said enclosure.

10. The filter of claim 9, wherein said filter means fits snugly in said second chamber.

11. The filter of claim 9, wherein said first chamber is positioned substantially vertically above said second chamber, and said filter means is spaced away from the sidewall of said second chamber.

* * * * *